United States Patent
Curiel et al.

(10) Patent No.: US 6,716,622 B2
(45) Date of Patent: Apr. 6, 2004

(54) TISSUE-SPECIFIC SELF-INACTIVATING GENE THERAPY VECTOR

(75) Inventors: David T. Curiel, Birmingham, AL (US); Paul N. Reynolds, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 84 days.

(21) Appl. No.: 09/907,186

(22) Filed: Jul. 17, 2001

(65) Prior Publication Data

US 2002/0022018 A1 Feb. 21, 2002

Related U.S. Application Data

(60) Provisional application No. 60/219,242, filed on Jul. 18, 2000, now abandoned.

(51) Int. Cl.[7] .................. C12N 15/00; C12N 15/86; C12N 15/87; C07H 21/04
(52) U.S. Cl. .................. 435/320.1; 435/456; 435/462; 536/23.1; 536/24.1
(58) Field of Search .................. 514/44; 435/320.1, 435/455, 456, 462; 536/23.1, 24.1

(56) References Cited

U.S. PATENT DOCUMENTS 5,712,114 A * 1/1998 Mankovich et al. ....... 435/69.1
5,817,492 A * 10/1998 Saito et al. .............. 435/172.3

OTHER PUBLICATIONS

Dang et al., Gene therapy and translational cancer research, 1999, Clinical Cancer Research, vol. 5, pp. 471–474.*
Xu et al., Strategies for enzyme/prodrug cancer therapy, 2001, Clinical Cancer Research, vol. 7, pp. 3314–3324.*
Romano et al., Latest developments in gene transfer technology: Achievements, perspectives, and controversies over therapeutic applications, 2000, Stem Cells, vol. 18, pp. 19–39.*

Meng et al., Tumor suppressor genes as targets for cancer gene therapy, 1999. In:Gene Therapy of Cancer, Academic Press, pp. 3–20.*

Verma et al., Gene therapy–promises, problems and prospects, 1997, Nature, vol. 389, pp. 239–242.*

Sato et al., Enhanced and specific gene expression via tissue specific production of cre recombinase using adenovirus vector, 1998, Biochemical and Biophysical Research Communications, vol. 244, pp. 455–462.*

* cited by examiner

*Primary Examiner*—David Guzo
*Assistant Examiner*—Quang Nguyen
(74) *Attorney, Agent, or Firm*—Benjamin Aaron Adler

(57) ABSTRACT

The present invention provides a strategy that allows for selective switching off of both transgene and viral gene expression in tissues where such expression is undesirable. The present invention employs a vector containing a tissue specific promoter that drives expression of Cre recombinase gene in tissue where transgene expression is undesirable. As a result of Cre recombinase expression, the same or another vector that expresses the transgene in that tissue will be cut by the action of the Cre recombinase into several pieces due to LoxP sites that are strategically placed within the vector backbone. Consequently, unwanted transgene as well as viral gene expression are prevented.

5 Claims, 8 Drawing Sheets

TISSUE-SPECIFIC SELF-INACTIVATING GENE THERAPY VECTOR

CROSS-REFERENCE TO RELATED APPLICATION

This non-provisional patent application claims benefit of provisional patent application U.S. Ser. No. 60/219,242, filed Jul. 18, 2000, now abandoned.

FEDERAL FUNDING LEGEND

This invention was produced in part using funds obtained through grants from National Institutes of Health. Consequently, the federal government has certain rights in this invention.

BACKGROUND OF THE INVENTION

1. Field of the Invention

The present invention relates generally to the field of gene therapy vector design. More specifically, the present invention relates to a tissue-specific self-inactivating gene therapy vector.

2. Description of the Related Art

Adenoviral vectors possess a number of attributes that render them useful gene delivery vehicles for systemic gene therapy. In particular, the in vivo transduction efficiencies achievable with these agents are greater than with currently available alternative vector systems (1). Ideally, such a system would be designed so that systemically administered vector would home specifically to tumor target cells without ectopic infection of normal cells.

However, a major stumbling block to this approach is the fact that the majority of adenoviral vectors administered systemically are sequestered in the liver. Therefore measures that specifically control the distribution of delivered transgene expression must be superimposed on the basic vector for optimal applicability of adenoviral vectors.

Various approaches to this problem have been proposed, including imparting both transductional and transcriptional targeting properties to Ad vectors (2–7). Although targeting strategies can reduce hepatocyte transduction, the level of sequestration of vector to these cells is so great that this approach alone is insufficient to completely ameliorate ectopic gene expression. Tissue specific promoters may add a further degree of transgene expression selectivity but there are few of these that have been validated in vivo and all are subject to some degree of non-specific activation or "leakiness". This has several importance consequences, one of which is that many of the genes designed for cancer therapy—"suicide genes" in particular—are of limited practical application due to dose limiting toxicity of the transgene action in the liver.

Hence, even when vectors that have been modified so as not to recognize the native adenovirus receptor are used, ectopic transgene expression in non-target organs remains a potential problem. Additional complementary strategies that can be superimposed upon these systems are needed to afford an even greater measure of control. Thus, the prior art is deficient in a strategy to reduce ectopic transgene expression in adenovirus-mediated gene transfer. The present invention fulfills this longstanding need and desire in the art.

SUMMARY OF THE INVENTION

The present invention provides a strategy that deliberately switches transgene expression off at a site where transgene expression might otherwise be disadvantageous. LoxP sites are strategically placed in an adenovirus vector that carries the transgene. Cre recombinase recognizing these LoxP sites will cut this vector into pieces, thereby de-activates the vector in tissues and organs where the delivered transgene could potentially give rise to toxicity. The Cre recombinase gene operably linked to a tissue-specific promoter can be provided by a separate adenovirus vector or contained in the same vector that carries the transgene. To stop transgene expression in the liver, Cre recombinase is driven by a liver specific promoter.

The object of the present invention is to reduce undesirable transgene expression in non-targeted tissue. In one aspect of the present invention, there is provided a tissue-specific self-inactivating gene expression system comprises of: (i) an adenovirus vector comprising at least one LoxP sequence and a transgene operably linked to a promoter, wherein said transgene and said promoter are flanked by said LoxP sequences; and (ii) an adenovirus vector comprises of a Cre recombinase gene operably linked to a tissue-specific promoter.

In another embodiment of the present invention, there is provided a tissue-specific self-inactivating gene expression vector that contains (i) more than one LoxP sequence, (ii) a transgene operably linked to a promoter wherein the transgene and the promoter are flanked by LoxP sequences, and (iii) a Cre recombinase gene operably linked to a tissue-specific promoter.

In another aspect of the present invention, there are provided methods of reducing transgene expression in non-targeted tissue in an individual by administering a therapeutically effective amount of tissue-specific self-inactivating gene expression vectors disclosed herein.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1A:
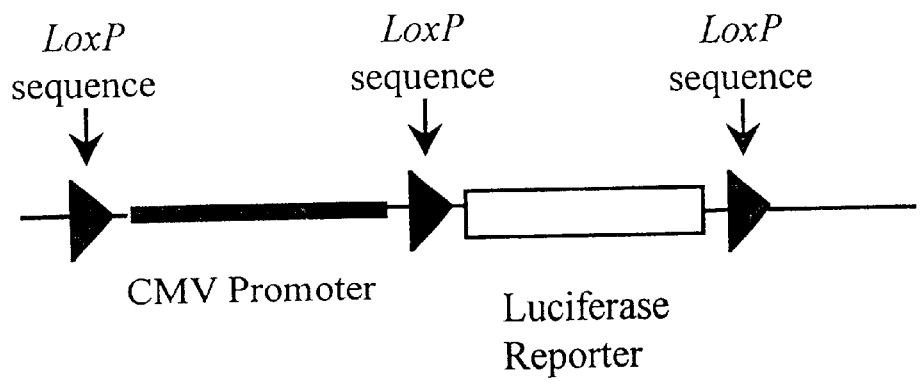
FIG. 1A shows the design of expression cassettes.

To complement strategies which primarily aim to ensure that transgene expression is sufficiently high in target tissues, the present invention focuses on a strategy to deliberately switch transgene expression off at a site where expression might otherwise be disadvantageous. With respect to adenovirus vector administration, the majority of vector localization and subsequent transgene expression (using nonselective promoters) is seen in the liver. Consequently, hepatotoxicity resulting from ectopic transgene expression is a major concern. In the context of cancer gene therapy using suicide genes for example, this toxicity has resulted in dose limiting morbidity and mortality in animal models (8–10). This problem is clearly an important issue in addition to concerns about residual expression of residual viral genes. Thus, an approach which switches transgene delivery off in the liver may improve the safety of suicide gene therapy.

Based on these considerations, the instant invention illustrates a "liver off" system. The approach uses the Cre recombinase (Cre)/LoxP system whereby the Cre enzyme catalyzes recombination at specific DNA sequences (LoxP sites). This technique has previously been used in the generation of transgenic knock-out mice and as an "on" switch in an adenovirus vector context by excising a DNA stuffer sequence inserted between promoters and transgenes (11–18). The utility of this system to effectively switch off the expression of an adenovirus-delivered transgene has not been reported. Thus, the present invention demonstrates that a system could be developed whereby the transgene expression resulting from adenovirus vectors containing LoxP flanked expression cassettes could be effectively switched off by the expression of a co-administered Cre gene which is under the control of a tissue-specific promoter.

As initial proof of principle, the present invention first develops a strategy that utilizes the Cre/LoxP system to switch off luciferase reporter gene expression, and evaluates efficacy both in vitro and in vivo. Data disclosed herein show that this approach can indeed inactivate transgene expression and importantly, the approach has efficacy in the liver in vivo.

The strategy described herein has enormous potential to improve upon current gene delivery technology. Every clinical application for which a systemically administerable therapy can be considered will benefit from this approach. This system will allow for the selective switching off of both transgene and viral gene expression in tissues in which such expression is undesirable. Although the first application of this strategy is to abolish this gene expression in the liver, this strategy will be adapted to turn off transgene expression in any chosen tissue, based on the selection of tissue specific promoters driving expression of Cre recombinase. Thus, this approach has broad application but will be especially relate to the delivery of "suicide genes" for cancer gene therapy, where unwanted hepatic expression leading to morbidity and mortality is well described.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

A "vector" is a replicon, such as plasmid, phage or cosmid, to which another DNA segment may be attached so as to bring about the replication of the attached segment.

A "replicon" is any genetic element (e.g., plasmid, chromosome, virus) that functions as an autonomous unit of DNA replication in vivo; i.e., capable of replication under its own control.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

In general, expression vectors containing promoter sequences which facilitate the efficient transcription of the inserted DNA fragment are used in connection with a host cell. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

Methods which are well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors.

It is also contemplated that pharmaceutical compositions may be prepared using the novel vector of the present invention. In such a case, the pharmaceutical composition comprises the novel vector of the present invention and a pharmaceutically acceptable carrier. A person having ordinary skill in this art would readily be able to determine, without undue experimentation, the appropriate dosages and routes of administration of the active component of the present invention. See Remington's Pharmaceutical Science, 17th Ed. (1990) Mark Publishing Co., Easton, Pa.; and *Goodman and Gilman's: The Pharmacological Basis of Therapeutics* 8th Ed (1990) Pergamon Press. When used in vivo for therapy, the active composition(s) of the present invention is administered to the patient or an animal in therapeutically effective amounts, i.e., amounts that eliminate or reduce the tumor burden.

The object of the present invention is to reduce undesirable transgene expression in non-targeted tissue. In one aspect of the present invention, there is provided a tissue-specific self-inactivating gene expression system comprises of: (i) an adenovirus vector comprising at least one LoxP sequence and a transgene operably linked to a promoter, wherein said transgene and said promoter are flanked by said LoxP sequences; and (ii) an adenovirus vector comprises of a Cre recombinase gene operably linked to a tissue-specific promoter. The promoter operably linked to the transgene can be a tissue-specific or tumor-specific promoter, and the transgene is a reporter gene or a therapeutic gene. Representative examples of useful therapeutic genes include the herpes simplex virus-thymidine kinase gene and *E. coli* cytosine deaminase gene. In one embodiment of the present invention, the tissue-specific promoter operably linked to the Cre recombinase gene is a liver-specific promoter.

In another embodiment of the present invention, there is provided a tissue-specific self-inactivating gene expression vector that contains (i) more than one LoxP sequence, (ii) a transgene operably linked to a promoter wherein the transgene and the promoter are flanked by LoxP sequences, and (iii) a Cre recombinase gene operably linked to a tissue-specific promoter. The promoter operably linked to the transgene can be a tissue-specific or tumor-specific promoter, and the transgene is a reporter gene or a therapeutic gene. Examples of the therapeutic gene include the herpes simplex virus-thymidine kinase gene and *E. coli* cytosine deaminase gene. In one embodiment of the present invention, the tissue-specific promoter operably linked to the Cre recombinase gene is a liver-specific promoter.

In another aspect of the present invention, there is provided a method of reducing transgene expression in non-targeted tissue in an individual in need of such treatment, comprising the step of: administering a therapeutically effective amount of an adenovirus vector comprises of more than one LoxP sequence and a transgene operably linked to a promoter, wherein said transgene and said promoter are flanked by said LoxP sequences; and administering a therapeutically effective amount of an adenovirus vector comprises of a Cre recombinase gene operably linked to a tissue-specific promoter, wherein said tissue-specific promoter drives the expression of Cre recombinase in said non-targeted tissue, thereby destroying said adenovirus vector expressing said transgene and reducing transgene expression in said non-targeted tissue. Generally, the individual has cancer Preferably, the tissue-specific promoter operably linked to the Cre recombinase gene is a liver-specific promoter, and the promoter operably linked to the transgene is a tissue-specific or tumor-specific promoter. The transgene is a reporter gene or a therapeutic gene. When the therapeutic gene used is the herpes simplex virus-thymidine kinase gene or *E. coli* cytosine deaminase gene, the individual is further treated with gancyclovir or 5-fluorocytosine, as is well known in the art.

In another embodiment of the present invention, there is provided a method of reducing transgene expression in non-targeted tissue in an individual by administering a therapeutically effective amount of tissue-specific self-inactivating gene expression vector that contains (i) more than one LoxP sequence, (ii) a transgene operably linked to a promoter wherein the transgene and the promoter are flanked by LoxP sequences, and (iii) a Cre recombinase gene operably linked to a tissue-specific promoter, wherein said tissue-specific promoter drives the expression of Cre recombinase in said non-targeted tissue, thereby destroying said expression vector and reducing transgene expression in said non-targeted tissue. Generally, the individual has cancer. Preferably, the tissue-specific promoter operably linked to the Cre recombinase gene is a liver-specific promoter, and the promoter operably linked to the transgene is a tissue-specific or tumor-specific promoter. The transgene is a reporter gene or a therapeutic gene. When the therapeutic gene used is the herpes simplex virus-thymidine kinase gene or *E. coli* cytosine deaminase gene, the individual is further treated with gancyclovir or 5-fluorocytosine.

The following examples are given for the purpose of illustrating various embodiments of the invention and are not meant to limit the present invention in any fashion.

EXAMPLE 1

Cre Inactivates LoxP Flanked Luciferase Expression Cassette

The feasibility of using the Cre/LoxP system to specifically inactivate a delivered transgene was evaluated first. A plasmid containing the cytomegalovirus (CMV) promoter and the luciferase reporter gene interspersed with LoxP sequences was constructed (pLCLLL, FIG. 1A). The cytomegalovirus promoter was inserted into the EcoRV site between the LoxP sequences of plasmid pBS246 (GibcoBRL). CMV-LoxP was then excised as a SmaI/MscI fragment and inserted into the SmaI site of the luciferase reporter gene plasmid PGL3, basic (Promega). CMV-LoxP-Luc was excised using KpnI and SalI, blunted and inserted into the EcoRV site of pBS246, thus forming plasmid pLCLLL which was used for initial in vitro analysis. The plasmid pBS185 containing the Cre recombinase gene under the control of the cytomegalovirus promoter was obtained from GibcoBRL. The plasmid pCMVpA containing the cytomegalovirus promoter and a poly A signal but no transgene was used as a control.

Figure 1B:
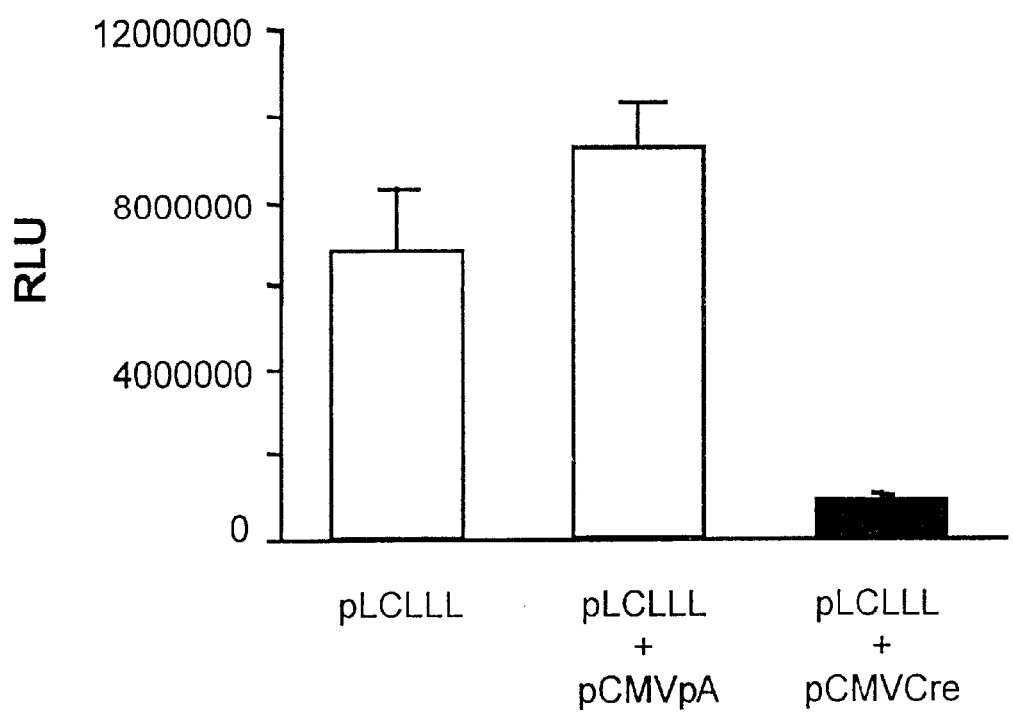
FIG. 1B shows Cre inactivates LoxP flanked luciferase expression cassette. HepG2 cells were transfected with pLCLLL plasmid alone or with pCMVpA control plasmid or pBS185 (expressing Cre recombinase) using Superfect (Qiagen) according to the manufacturers instructions. HepG2 cells were propagated in RPMI (GibcoBRL) medium supplemented with 10% fetal calf serum, penicillin and streptomycin. Cells were plated at $1\times10^5$ cells per well in 12 well plates. The next day, cells were transfected using a total of 2.5 µg of plasmid per triplicate wells. Forty eight hours after transfection a luciferase assay using a Luciferase Assay System kit (Promega) was performed according to the manufacturer's instructions. Mean +/− SD of three experiments shown.

Initially, the ability of Cre recombinase to inactivate the expression cassette in a human liver cell line was investigated. For these studies, HepG2 cells (American Type Culture Collection) were transfected with either pLCLLL alone or in combination with pBS185 (expressing Cre recombinase), or the control plasmid pCMVpA. FIG. 1B shows that the combination of pBS185 and pLCLLL resulted in a mean 87±2% (mean±SD of three experiments) reduction in luciferase expression compared to pLCLLL alone, or 91±0.8% compared to pLCLLL+pCMVpA ($p<0.01$ by t-test), thus confirming the basic premise that an expression cassette could be inactivated in this way.

EXAMPLE 2

Cre Inactivation System in Adenovirus Vector Context

Having established the functionality of the expression cassette described above, its functionality in the context of adenoviral vectors was then evaluated. An E1/E3 deleted adenoviral vector (AdLCLLL) containing the LoxP flanked luciferase cassette was constructed using the AdEasy system (19). The LCLLL segment was excised as a NotI fragment, inserted into the NotI site of the adenoviral shuttle plasmid pShuttle. The adenoviral genome was constructed by homologous recombination with pAdEasy I in BJ5183 cells by standard techniques, then the virus was generated by transfection of the linearized genome into 911 cells. After confirmation of construct by analysis of viral DNA, stocks of virus were generated in 293 cells and quantified by standard plaque assay and optical density titers. AdCMVCre, an adenoviral vector carrying the Cre recombinase gene, has been previously described, as has AdCMVHSV-TK which was used as a control vector (18, 20).

Figure 2A:
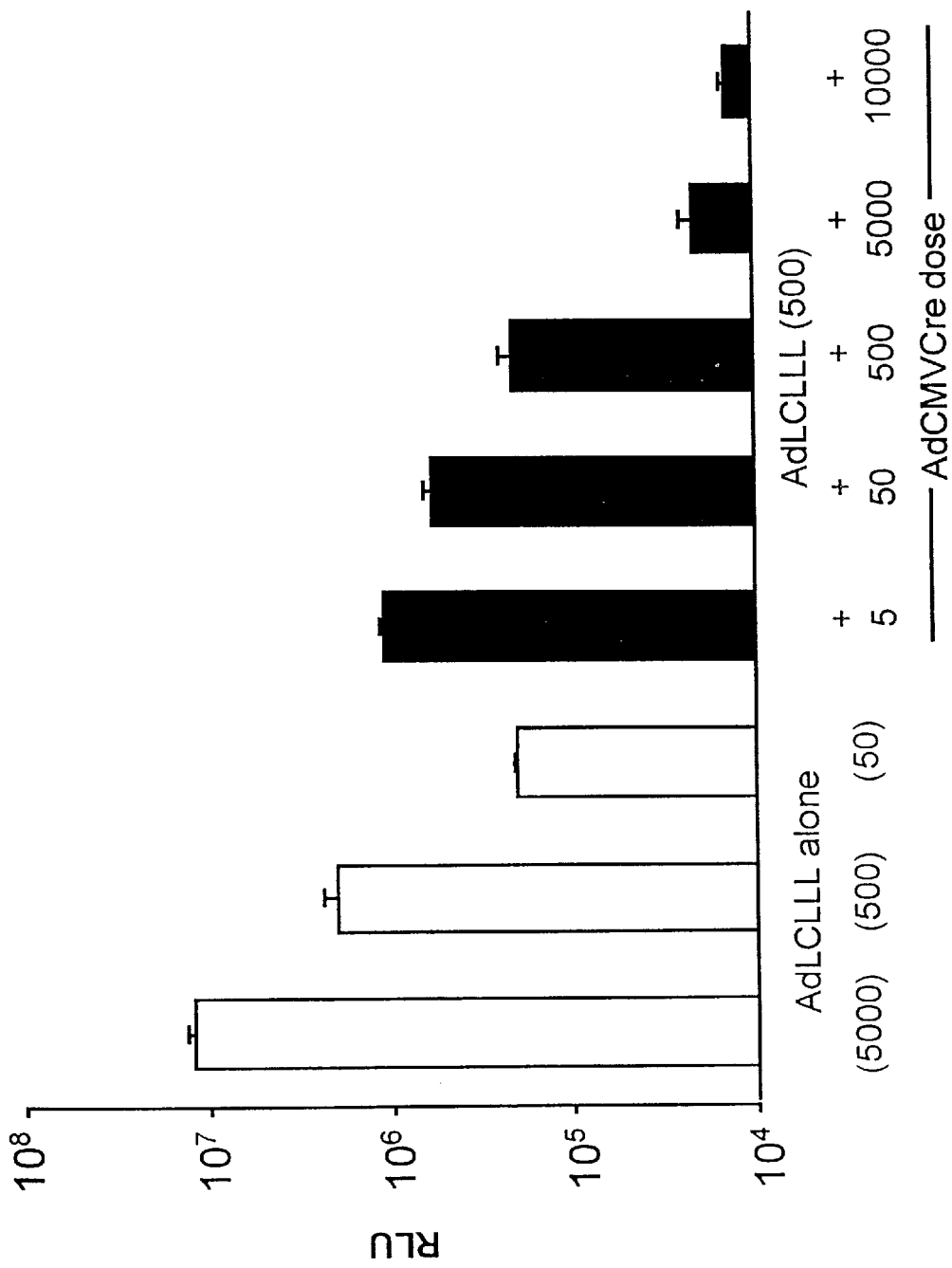
FIG. 2A shows Cre recombinase inactivation of luciferase in adenoviral vector. HepG2 cells were infected with AdL- CLLL alone (open bars) or with AdCMVCre (solid bars). Numbers on x-axis refer to dose of viral particles per cell. Cells were plated at 50,000 per well in 24 well plates. Cells were infected next day with viruses as shown in culture medium containing 2% FCS. After one hour the medium was removed and cells were washed with PBS and then cultured in complete medium for a further 24 hours. Luciferase assay was then performed. Results shown are representative of two separate experiments. Mean of triplicate determinations.
Figure 2B:
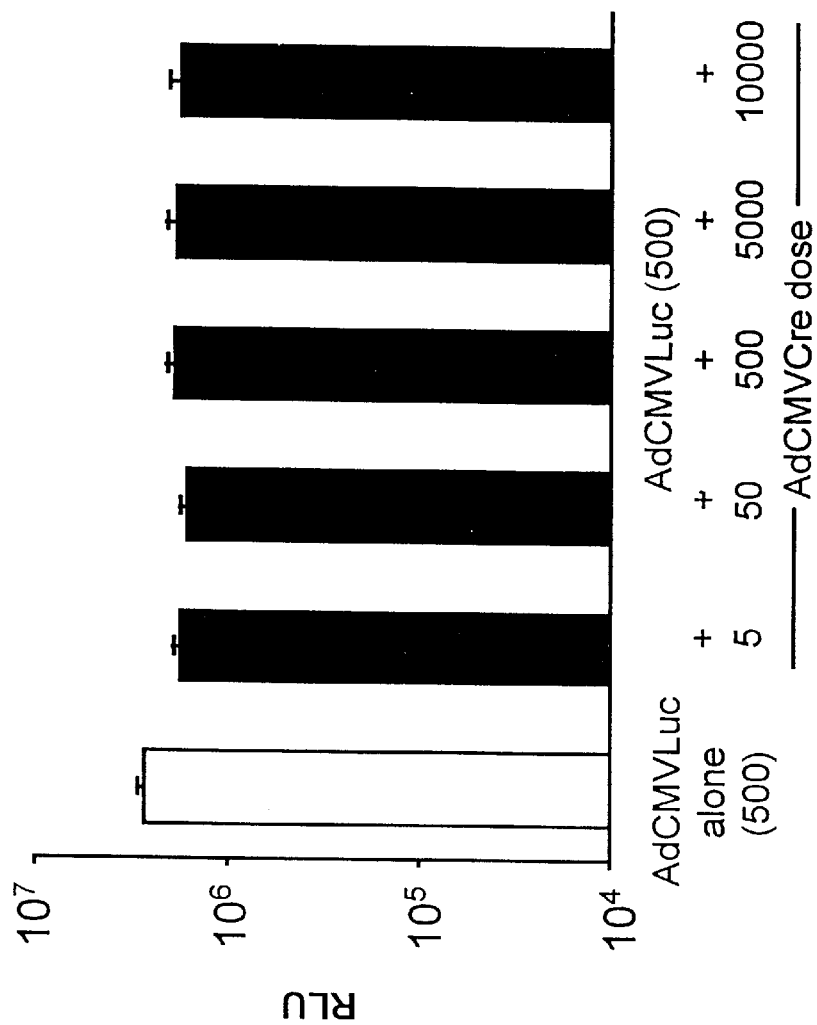
FIG. 2B shows AdCMVCre infection did not inactivate luciferase expression from the vector AdCMVLuc that has no LoxP sites.

To assess the system in adenoviral vectors, HepG2 cells were infected with AdLCLLL at a dose of 50, 500 or 5000 viral particles per cell (to demonstrate a dose-response relationship) as well as 500 viral particles per cell in combination with various doses of AdCMVCre (FIG. 2). An adenoviral vector containing the CMV promoter driving luciferase expression (with no LoxP sequences) was used as a control. It was found that the combination of AdLCLLL with AdCMVCre resulted in a dose dependant reduction in luciferase expression (FIG. 2A), whereas AdCMVCre infection did not significantly reduce the luciferase expresion from AdCMVLuc (FIG. 2B). In this experiment, the combination of equal particle numbers of AdLCLLL and AdCMVCre led to a reduction in transgene expression equivalent to that seen when the dose of AdLCLLL alone was reduced by 10-fold. Maximum reduction, seen with the highest dose of AdCMVCre used, was by over 99%. Thus, the feasibility of using the Cre/LoxP system to inactivate adenovirally delivered genes was shown.

Figure 3:
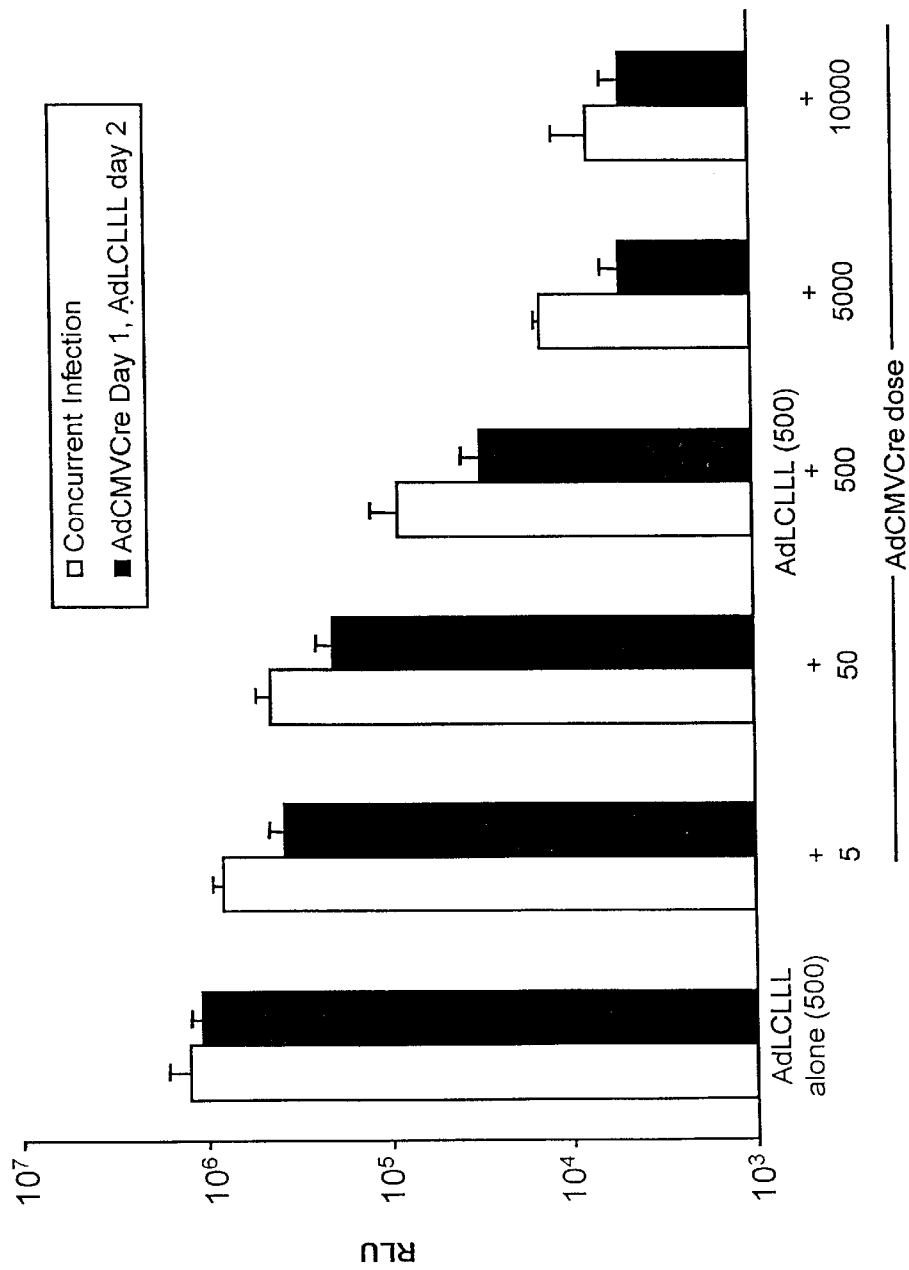
FIG. 3 shows improved effectiveness of Cre inactivation concept by temporal separation of infections. HepG2 cells were infected with AdLCLLL with or without various doses of AdCMVCre at 0 or 24 hours after AdCMVCre infection. Luciferase assay w as performed 24 hours after AdLCLLL infection. Numbers on x-axis refer to dose of viral particles per cell. Mean +/− of triplicate determinations.

The system was further evaluated to determine the effect of infecting cells first with AdCMVCre 24 hours before infecting with AdLCLLL, thus allowing time for Cre recombinase to be generated before the arrival of the LoxP flanked cassette. In a direct comparison of concurrent infection versus temporal separation of infection, greater reduction in luciferase expression was seen when the AdCMVCre was given first (FIG. 3). Further temporal manipulations may be optimized depending on the application and may thus allow greater reductions in transgene levels, if required.

Figure 4:
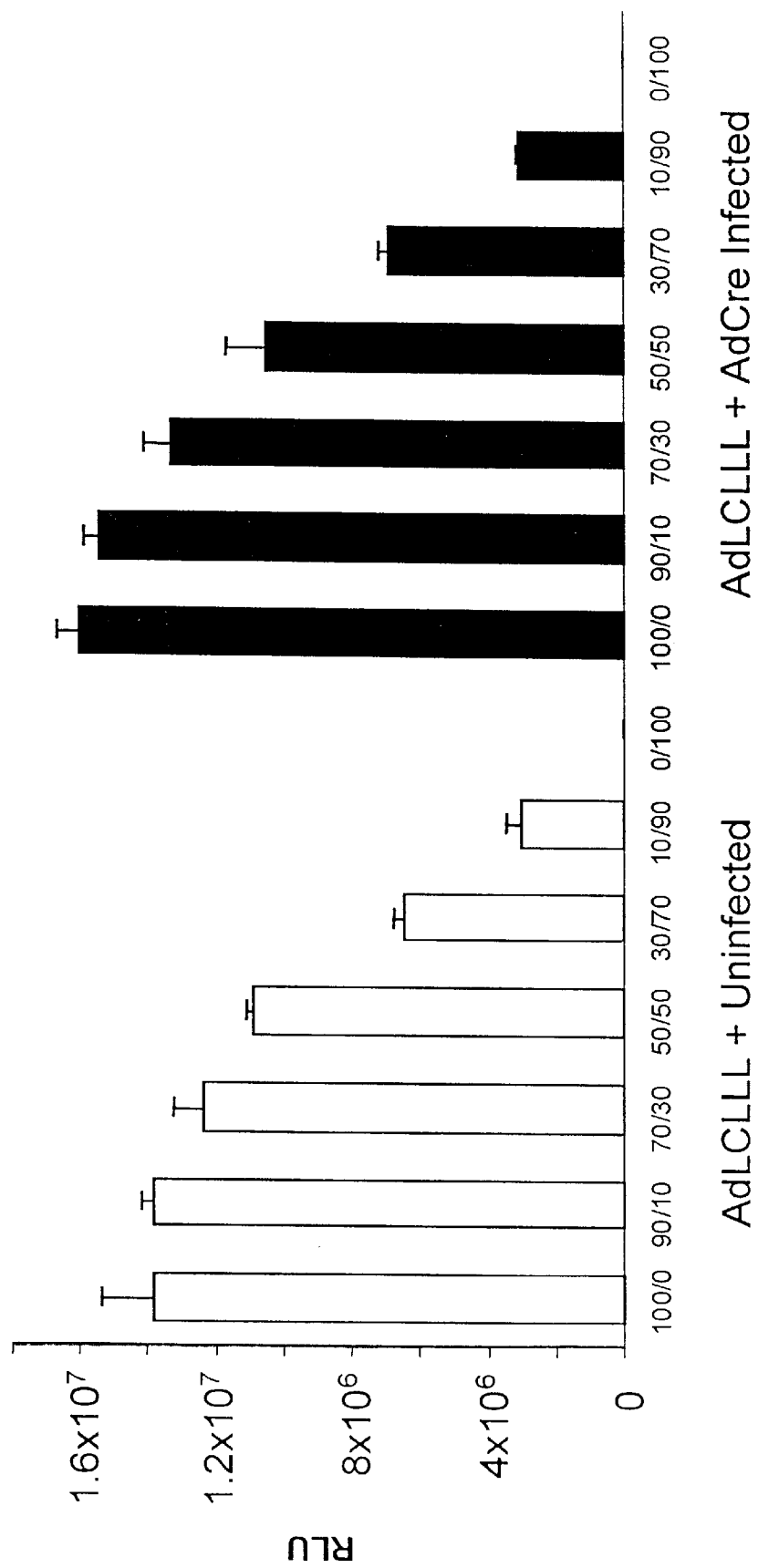
FIG. 4 shows no evidence of bystander effect from cells expressing Cre. HepG2 cells infected with AdLCLLL were mixed with uninfected or AdCMVCre infected cells 24 hours later in the proportions shown. Luciferase analysis was performed 24 hours after mixing.

The system was also examined for evidence of a bystander effect of Cre-expressing cells on adjacent AdLCLLL expressing cells. HepG2 cells were infected separately with either AdCMVCre or AdLCLLL, then the AdLCLLL infected cells were mixed at various ratios with either uninfected or AdCMVCre infected cells 24 hours later. As expected, the amount of luciferase expression decreased as the proportion of AdLCLLL cells decreased. However, this decrease was the same whether the other cells were uninfected or whether they expressed Cre (FIG. 4). Thus no bystander effect was observed. This finding may be advantageous in that the control of the "off" switch should be tightly restricted only to those cells that are infected with AdCMVCre.

EXAMPLE 3

Cre Inactivation System in vivo

Figure 5A:
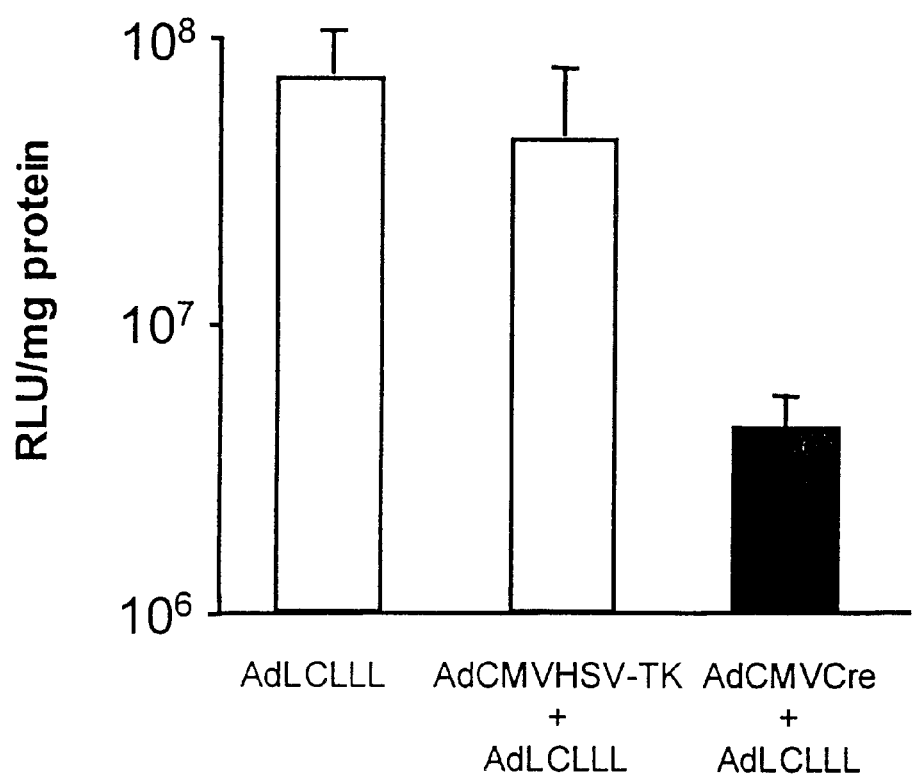
FIG. 5A shows in vivo effectiveness of liver untargeting concept. Adenoviral vectors were administered by tail vein injection (total volume 200 µl) into female C57/BL6 mice (n=3) aged 6–8 weeks (Charles Rivers). AdCMVCre or control (PBS or AdCMVHSV-TK) was administered on day 1, then AdLCLLL on day 2, and animals sacrificed on day three. Livers were harvested, snap frozen in ethanol/dry ice, ground to a fine powder using a mortar and pestle sitting in an ethanol/dry ice bath. The powders were assayed for luciferase activity using the Promega Luciferase Assay System kit.
Figure 5B:
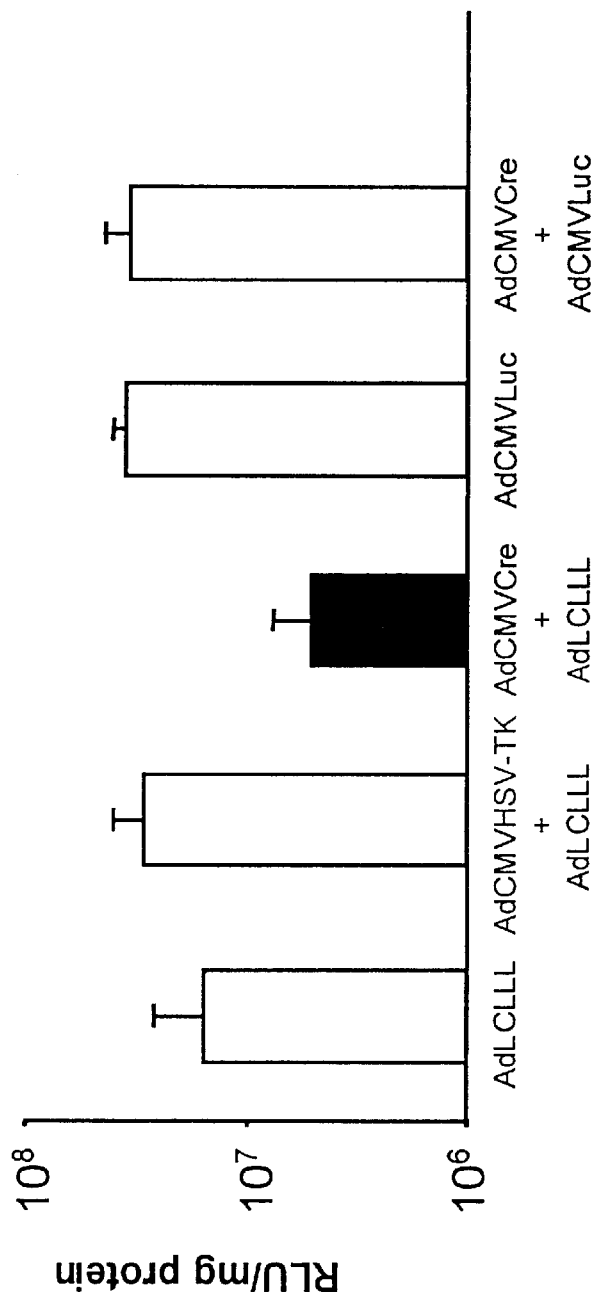
FIG. 5B includes additional control of AdCMVluc showing no effect of AdCMVCre pre-treatment. (n=4 per group).

The entire rationale for proposing an expression cassette inactivation strategy was to investigate its potential in vivo, especially in the critical context of liver transgene expression. Thus, in vivo experiments combining AdLCLLL and AdCMVCre were conducted to determine the effect on transgene expression. Animal studies were approved by the University of Alabama Institutional Animal Use and Care Committee. Mice were injected by tail vein on day one with either PBS as a control, AdCMVCre ($2\times10^{10}$ viral particles) or AdCMVHSV-TK ($2\times10^{10}$ particles) which served as an irrelevant virus control. On day two, mice where injected with AdLCLLL ($2\times10^{10}$ particles), then on day four the mice were sacrificed to harvest the livers and examine the transgene expression (FIG. 5A). Approximately one log reduction in transgene expression was seen with the AdCMVCre+AdLCLLL combination whereas no significant reduction was seen with the control combination. Furthermore, no reduction in luciferase expression was seen with the AdCMVCre+AdCMVLuc combination compared to AdCMVLuc alone (FIG. 5B).

Figure 5C:
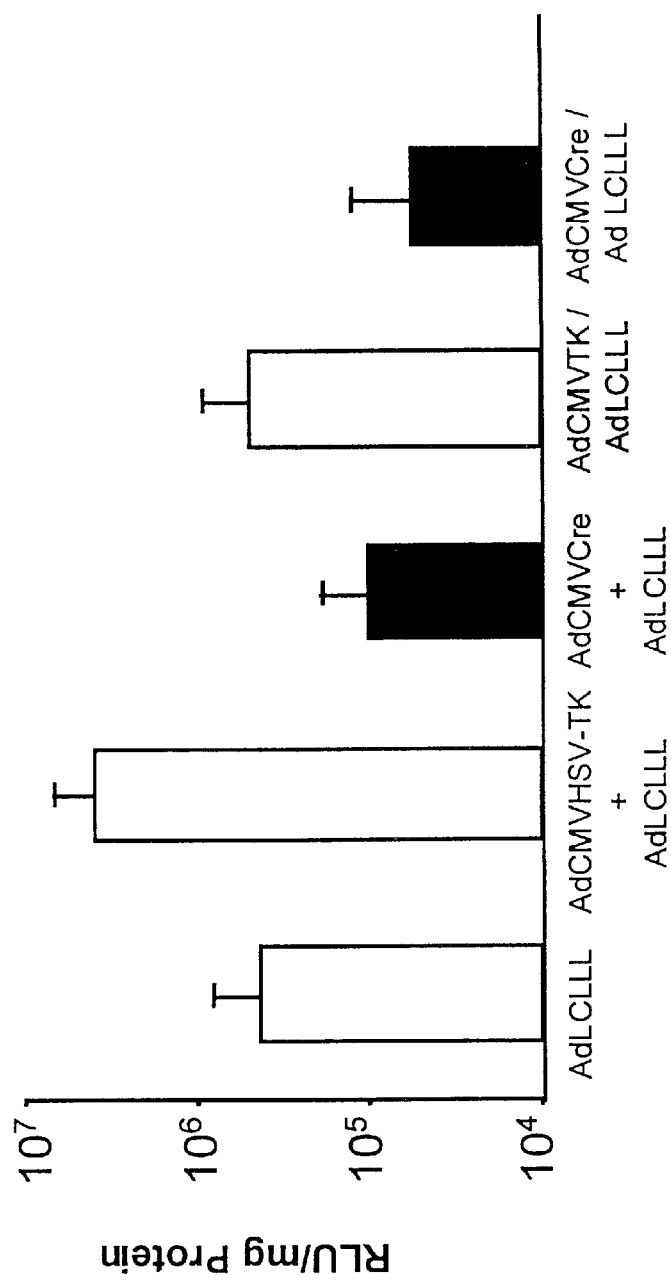
FIG. 5C further repeat experiment using Balb C mice, n=3 per group. Last two bars represent administration of AdLCLLL together with either AdCMVHSV-TK or AdCMVCre as one injection. In each case bars=mean +/− SD.

In a separate experiment, the effects of co-administering AdCMVCre with AdLCLLL on the same day as well as sequentially were evaluated (FIG. 5C). Here again, a reduction in luciferase expression was seen with the AdCMVCre/AdLCLLL combination, but not with the control AdCMVHSV-TK/AdLCLLL combination. In each experiment using C57BL6 mice, $p<0.04$ (by Student's t-test) comparing the logarithmically transformed data from the groups AdCMVCre+AdLCLLL vs AdHSVTK+AdLCLLL. More variability was seen in experiment with BALB/C mice, although the difference between the AdCMVCre+AdLCLLL and the control combination was still apparent. The incorporation of the relevant controls (irrelevant virus in place of AdCMVCre, and the non-LoxP containing AdCMVLuc in place of AdLCLLL) clearly shows that the effects are specific for the Cre/LoxP combination, and not due either to the potential induction of anti-Ad immune responses or non-specific toxicity related to AdCMVCre. Thus, these data show that the inactivating vector strategy of the present invention does indeed have functionality in vivo.

Efforts to achieve improved control of gene expression via improvements in basic vector design have been a major focus of gene therapy research in recent years. These approaches have principally focused on modifying either the transduction properties of vectors via tropism modification, or the gene expression profile of delivered transgenes via the use of tissue specific promoters. For the greatest possible control to be achieved, it is likely that some combination of targeting approaches will be required. The strategy disclosed in the present invention represents a further complementary approach, especially in those situations were ectopic transgene expression may be toxic. In addition, it would be feasible to add additional LoxP sites in other areas of the Ad genome, thereby potentially inactivating not only transgene expression but also ectopic expression of residual native viral genes. Furthermore, optimization may be possible with respect to dose and timing of the two vectors; but importantly, data presented above have demonstrated that the approach has potential use in vivo.

In its present form the approach may have utility in situations where potentially toxic transgenes are administered in a loco-regional context for tumor therapy. In this regard, administration of adenoviral vectors carrying the HSVTK transgene into the peritoneum has lead to ectopic transduction of hepatocytes, resulting in dose limiting hepatic toxicity upon gancyclovir administration (10). Pretreatment by intravenous injection of AdCMVCre that leads to hepatic Cre expression would protect the liver from the toxicity of a peritoneally administered adenoviral vector carrying a LoxP flanked HSVTK gene. The key principle is to have Cre expression being dominant at the site to be protected, and the therapeutic gene dominating at the treatment site.

As transductional and transcriptional targeting strategies evolve, further rational combinations can be envisaged. For instance, one adenoviral vector carrying a LoxP flanked therapeutic gene could be transductionally targeted to tumor upon intravenous administration, whereas a second vector having native tropism and carrying the Cre recombinase gene would preferentially go to the liver, thereby reducing any ectopic transgene expression that may have arisen due to incomplete specificity of the transductional targeting.

In it's present form, the lack of a bystander effect indicates the need for co-infection of the one cell for the inactivation strategy to work. To reduce potential inefficiencies resulting from this restriction, Cre recombinase could be placed under the control of a liver specific promoter. Such an approach could then allow for the derivation of single vectors possessing two cassettes—one having a tumor specific promoter driving a LoxP flanked therapeutic gene, the other having a liver specific promoter driving Cre. Such a system would therefore avoid a net increase in the total adenoviral vector administration needed with the current approach. Furthermore, the use of conditionally replicative adenoviral agents has received considerable attention recently and has shown promise as a cancer therapy (21). Incorporation of a Cre/LoxP control system might also offer improved safety in this setting.

In summary, the application of the Cre/LoxP system described herein provides a basis for a multitude of potential applications to significantly improve the utility and safety of adenovirally delivered transgenes.

The following references were cited herein:
1. Brody and Crystal. *Ann NY Acad Sci* (1994) 716: 90–101.
2. Reynolds et al. *Molecular Therapy* (1999) In Press
3. Douglas et al. *Nat Biotech* (1996) 14: 1574–1578.
4. Dmitriev et al. *J Virol* (1998) 72: 9706–9713.
5. Wickham et al. *J Virol* (1997) 71: 8221–8229.
6. Adachi et al. *Cancer Res* (2000) 60: 4305–10.
7. Koeneman et al. *World J Urol* (2000) 18: 102–10.
8. Gao et al. *J Virol* (1996) 70: 8934–43.
9. Brand et al. *Cancer Gene Ther* (1997) 4: 9–16.
10. van der Eb et al. *Gene Ther* (1998) 5: 451–8.
11. Lakso et al. *Proc Natl Acad Sci USA* (1996) 93: 5860–5.
12. Ramirez-Solis et al. *Nature* (1995) 378: 720–4.
13. Wang et al. *Proc Natl Acad Sci USA* (1996) 93: 3932–6.
14. Sakai et al. *Biochem Biophys Res Commun* (1995) 217: 393–401.
15. Lewandoski and Martin. *Nat Genet* (1997) 17: 223–5.
16. Okuyama et al. *Gene Ther* (1998) 5: 1047–53.
17. Bilbao et al. *Transplant Proc* (1999) 31: 792–3.
18. Arafat et al. *Mol Ther* (2000) 1: 545–54.
19. He et al. *Proc Natl Acad Sci USA* (1998) 95: 2509–14.
20. Rancourt et al. *Clin Cancer Res* (1998) 4: 2455–2461.
21. Alemany et al. *Nat Biotechnol* (2000) 18: 723–727.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A tissue-specific self-inactivating gene expression system comprising:
   (i) an adenovirus vector comprising at least three LoxP sequences and a transgene operably linked to a promoter, wherein each of said transgene and said promoter is flanked by said LoxP sequences; and
   (ii) an adenovirus vector comprising a Cre recombinase gene operably linked to a tissue-specific promoter, wherein said tissue-specific promoter drives the expression of said Cre recombinase in a tissue, thereby destroying said adenovirus vector expressing said transgene and reducing the expression of said transgene in said tissue.

2. The gene expression system of claim 1, wherein said promoter operably linked to the transgene is selected from the group consisting of a tissue-specific promoter and a tumor-specific promoter.

3. The gene expression system of claim 1, wherein said transgene is selected from the group consisting of a reporter gene and a therapeutic gene.

4. The gene expression system of claim 3, wherein said therapeutic gene is selected from the group consisting of a herpes simplex virus-thymidine kinase gene and a *E. coli* cytosine deaminase gene.

5. The gene expression vector of claim 1, wherein said tissue-specific promoter operably linked to the Cre recombinase gene is a liver-specific promoter.

* * * * *